United States Patent [19]

Carr et al.

[11] Patent Number: 5,137,886
[45] Date of Patent: Aug. 11, 1992

[54] INSECTICIDAL COMPOUNDS

[75] Inventors: Robin A. E. Carr, Royston; Donn W. Moseley, Reading; Nan C. Sillars, Kew Gardens, all of Great Britain

[73] Assignee: Imperial Chemical Industries PLC, Millbank, United Kingdom

[21] Appl. No.: 624,162

[22] Filed: Dec. 6, 1990

[30] Foreign Application Priority Data

Dec. 15, 1989 [GB] United Kingdom ............... 8928383.2

[51] Int. Cl.$^5$ ..................... A61K 31/44; C07D 413/12
[52] U.S. Cl. ............................. 514/237.2; 514/222.2; 514/226.8; 514/227.5; 514/228.8; 514/232.2; 514/235.5; 514/328; 514/347; 544/3; 544/55; 544/58.6; 544/60; 544/63; 544/96; 544/124; 544/130; 544/131; 546/294
[58] Field of Search ................. 544/131, 3, 55, 58.6, 544/60, 63, 96, 124, 130; 514/235.5, 222.2, 226.8; 227.5, 228.8, 232.2, 237.2, 328, 347; 546/294

[56] References Cited

U.S. PATENT DOCUMENTS

| | | | |
|---|---|---|---|
| 3,954,782 | 5/1976 | Fleckenstein et al. | 544/131 |
| 3,956,294 | 5/1976 | Fleckenstein et al. | 544/131 |
| 3,980,659 | 9/1976 | Fleckenstein et al. | 544/131 |
| 4,061,642 | 12/1977 | Fleckenstein et al. | 544/131 |
| 4,987,141 | 1/1991 | Bushell et al. | 514/346 |

FOREIGN PATENT DOCUMENTS

| | | |
|---|---|---|
| 160436 | 11/1985 | European Pat. Off. |
| 182603 | 5/1986 | European Pat. Off. |
| 222608 | 5/1987 | European Pat. Off. |
| 227601 | 7/1987 | European Pat. Off. |
| 1570863 | 6/1969 | France |

OTHER PUBLICATIONS

Kato et al., Chemical Structures & Insecticidal Activity of 3-Alkylthiophenyl Alkanesulfonates, J. Pesticide Sci. 13, 107-115 (1988).
C.A., vol. 71, No. 23, Dec. 8, 1969; abstract No. 112994z.
C.A., vol. 81, No. 7, Aug. 19, 1974; abstract No. 34590e.
C.A., vol. 86, No. 15, Apr. 11, 1977, abstract No. 106084w.
C.A., vol. 102, No. 19, May 13, 1985, abstract No. 166504s.
C.A., vol. 111, No. 25, Dec. 18, 1989, abstract No. 232866a.

*Primary Examiner*—Carolyn Elmore
*Assistant Examiner*—Brian M. Burn
*Attorney, Agent, or Firm*—Lynn Marcus-Wyner

[57] ABSTRACT

The invention provides insecticidally active compounds of formula (I):

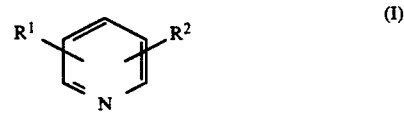

wherein X is nitrogen or carbon bearing a hydrogen atom; $R^1$ is a group of formula $-S(O)_n-Y$, wherein Y is an optionally substituted heterocyclic ring containing at least one nitrogen atom, the point of attachment of the group Y being at a ring nitrogen atom, and n is 0, 1 or 2; $R^2$ is a group of formula $-OSO_2R^3$ wherein $R^3$ is selected from $C_{1-8}$ alkyl, $C_{1-4}$ alkyl substituted by an optionally substituted phenyl or heterocyclic ring, $C_{1-8}$ haloalkyl, $C_{2-6}$ alkenyl, $C_{2-4}$ alkenyl substituted by an optionally substituted phenyl or heterocyclic ring, $C_{2-4}$ alkynyl, $C_{2-4}$ alkynyl substituted by an optionally substituted phenyl or heterocyclic ring, optionally substituted aryl, and a group of formula $-N(R^4)(R^5)$ wherein $R^4$ and $R^5$ are independently selected from hydrogen and $C_{1-6}$ alkyl or wherein $R^4$ and $R^5$ together represent $-(CH_2)_p-$ wherein p is 2, 3, 4 or 5; and wherein the groups $R^2$ and $R^1$ occupy either a 1,3 configuration relative to each other on the ring when X is carbon bearing a hydrogen, or a 2,4 or 2,6 configuration relative to the group X when X is nitrogen.

The invention also provides compositions comprising the compounds of formula (I) and methods of their use in combating insect pests, and novel intermediates and chemical processes for their preparation.

14 Claims, No Drawings

INSECTICIDAL COMPOUNDS

This invention relates to novel insecticidally active compounds, to compositions comprising them and methods of their use in combating insect pests, and to novel intermediates and chemical processes useful in their preparation.

Insecticidal activity has been reported for alkylthiophenyl sulphonates and oxidised derivatives in Japanese Patent Publication J68/003898 and in Japanese Patent Application No J48/098025, and also by Kato et al in Journal of Pesticide Science, Volume 13, pages 107–115 (1988). Insecticidal and nematocidal activity has also been described for alkylthiopyrid-2-yl sulphonates and oxidised derivatives in European Patent Application Nc 0182603. The present invention is based on the discovery of high levels of insecticidal activity for novel pyridyl and phenyl sulphonates having a sulphonamide substituent, or a reduced form thereof, on the pyridine or benzene ring such that the two substituents are arranged in a 1,3-configuration relative to each other. The compounds of the invention exhibit particularly high levels of control of target insect pests and are characterised by an excellent level of systemic activity In a first aspect the invention provides a compound of formula (I):

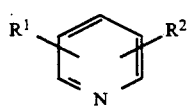

(I)

wherein X is nitrogen or carbon bearing a hydrogen atom; $R^1$ is a group of formula $—S(O)_n—Y$, wherein Y is an optionally substituted heterocyclic ring containing at least one nitrogen atom, the point of attachment of the group Y being at a ring nitrogen atom, and n is 0, 1 or 2; $R^2$ is a group of formula $—OSO_2R^3$ wherein $R^3$ is selected from $C_{1-8}$ alkyl, $C_{1-4}$ alkyl substituted by an optionally substituted phenyl or heterocyclic ring, $C_{1-8}$ haloalkyl, $C_{2-6}$ alkenyl, $C_{2-4}$ alkenyl substituted by an optionally substituted phenyl or heterocyclic ring, $C_{2-4}$ alkynyl, $C_{2-4}$ alkynyl substituted by an optionally substituted phenyl or heterocyclic ring, optionally substituted aryl, and a group of formula $—N(R^4)(R^5)$ wherein $R^4$ and $R^5$ are independently selected from hydrogen and $C_{1-6}$ alkyl or wherein $R^4$ and $R^5$ together represent $—(CH_2)_p—$ wherein p is 2, 3, 4 or 5; and wherein the groups $R^2$ and $R^1$ occupy either a 1,3 configuration relative to each other on the ring when X is carbon bearing a hydrogen, or a 2,4 or 2,6 configuration relative to the group X when X is nitrogen.

The terms alkyl, haloalkyl, alkoxy, alkoxyalkyl, alkanoyl, alkenyl and alkynyl as used herein include within their scope both straight and branched chain varieties. The term aryl as used herein includes within its scope aromatic five- and six-membered carbocyclic or heterocyclic rings, or fused systems comprising two or more of such rings, characterised by delocalisation bonding electrons over all of the constituent atoms of the ring. Suitable examples are phenyl, pyridyl, pyrimidinyl, furyl, thienyl, pyrazolyl, pyrazinyl, pyridazinyl, imidazolyl, thiazolyl, naphthyl, indolyl, benzofuryl, quinolinyl, isoquinolinyl and benzothienyl. The term optionally substituted as used herein includes within its scope substitution by one or more substituents which may be the same or different and which will typically be selected from alkyl, alkenyl, alkynyl, halo, nitro, cyano, hydroxy, acyl, acyloxy, thio, alkylthio, amino, alkylamino, dialkylamino, alkoxy, alkoxycarbonyl, amido, N-alkylamido, oxo and others.

Suitable examples of the group Y are optionally substituted heterocycles containing one nitrogen atom at the point of attachment, for example piperidin-1-yl, pyrrolidin-1-yl, pyrrol-1-yl, 3-pyrrolin-1-yl, azetidin-1-yl, aziridin-1-yl, pyrrolidin-2,4-dione-1-yl, 3-pyrrolin-2,4-dione-1-yl or piperidin2,6-dione-1-yl, and optionally substituted heterocycles containing one nitrogen atom at the point of attachment and at least one other heteroatom, for example pyrazol-1-yl, imidazol-1-yl, tetrazol-2-yl, tetrazol-1-yl, morpholin-4-yl, thiomorpholin-4-yl, oxazolidin-3-yl, oxazolidin-2-one-3-yl, 1,2,3-triazol-1-yl, 1,2,3-triazol-2-yl, 1,2,4-triazol-1-yl or 1,2,4,-triazol-4-yl.

Particularly preferred compounds according to the invention are those for which the group Y is a 4-, 5- or 6-membered heterocycle containing one nitrogen at the point of attachment and, optionally, one other heteroatom selected from oxygen and sulphur, for example morpholin-4-yl, piperidin-1-yl, thiomorpholin-4-yl, pyrrolidin-1-yl, azetidin-1-yl, or pyrrol-1-yl.

Suitable examples of the group $R^3$ are $C_{1-4}$ alkyl, for example methyl, ethyl, n-propyl, 1-methylethyl, n-butyl, 2-methylpropyl or 1,1-dimethylethyl; $C_{1-2}$ alkyl substituted with an optionally substituted phenyl group, for example phenylmethyl or 2-phenylethyl; $C_{1-6}$ haloalkyl, for example fluoromethyl, difluoromethyl, trifluoromethyl, chloromethyl, dichloromethyl, trichloromethyl, 2,2,2-trifluoroethyl, 1,1,2,2,2- pentafluoroethyl, 2,2,2-trichloroethyl, 3-chloropropyl, 3-fluoropropyl, or perfluoro-n-hexyl; $C_{2-4}$ alkenyl, for example ethenyl or prop-2-en-1-yl; ethenyl optionally substituted with an optionally substituted phenyl group, for example 2-phenylethenyl; optionally substituted phenyl, for example phenyl or a 4-substituted phenyl group such as 4-chlorophenyl, 4-bromophenyl, 4-fluorophenyl, 4-methylphenyl, 4-trifluoromethylphenyl or 4-methoxyphenyl; optionally substituted pyridyl, for example pyrid-2-yl or 6-fluoro-2-pyridyl; 2-thienyl; 3-thienyl; or a group of formula $—N(R^4)(R^5)$, wherein $R^4$ and $R^5$ are independently selected from hydrogen and $C_{1-6}$ alkyl, for example methylamino, ethylamino, dimethylamino or diethylamino, or wherein $R^4$ and $R^5$ together represent $—(CH_2)_p—$, wherein p is 2, 3, 4 or 5, for example pyrrolidin-1-yl or piperidin-1-yl.

A preferred group of compounds according to the invention comprises any of those compounds of formula (I) described hereinabove wherein the value of n is 2. A further preferred group of compounds according to the invention comprises any of those compounds of formula (I) described hereinabove wherein the group X is nitrogen.

A further preferred group of compounds according to the invention are those of formula (I) described hereinabove wherein the groups $R^2$ and $R^1$ occupy a 2,6-configuration relative to the group X.

A further preferred group of compounds according to the invention are those of formula:

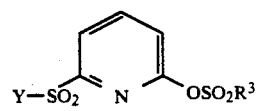

wherein Y is selected from pyrrol-1-yl, morpholin-4-yl, thiomorpholin-4-yl, piperidin-1-yl, pyrrolidin-1-yl and azetidin-1-yl, and $R^3$ is selected from $C_{1-6}$ alkyl, $C_{1-6}$ haloalkyl and a group of formula $-N(R^4)(R^5)$ where $R^4$ and $R^5$ are independently selected from hydrogen and $C_{1-4}$ alkyl.

Examples of compounds according to this invention which are to be considered as being specifically disclosed herein are shown in Tables IA, IB and IC.

TABLE IA

Y—(O)$_n$S— [pyridine ring] —OSO$_2$R$^3$

| Compound No | Y | n | R$^3$ |
|---|---|---|---|
| 1 | morpholin-4-yl | 2 | CH$_3$ |
| 2 | azetidin-1-yl | 2 | CH$_3$ |
| 3 | piperidin-1-yl | 2 | CH$_3$ |
| 4 | pyrrol-1-yl | 2 | CH$_3$ |
| 5 | pyrrolidin-1-yl | 2 | CH$_3$ |
| 6 | imidazol-1-yl | 2 | CH$_3$ |
| 7 | 1,2,3,4-tetrazol-2-yl | 2 | CH$_3$ |
| 8 | 1,2,4-triazol-1-yl | 2 | CH$_3$ |
| 10 | 2-oxo-1,3-oxazolidin-3-yl | 2 | CH$_3$ |
| 11 | 2,6-dioxopiperidin-1-yl | 2 | CH$_3$ |

TABLE IA-continued

Y—(O)$_n$S— [pyridine ring] —OSO$_2$R$^3$

| Compound No | Y | n | R$^3$ |
|---|---|---|---|
| 12 | 2,5-dioxopyrrolidin-1-yl | 2 | CH$_3$ |
| 13 | 2,5-dioxo-2,5-dihydropyrrol-1-yl (maleimido) | 2 | CH$_3$ |
| 14 | morpholin-4-yl | 2 | 4-CH$_3$-C$_6$H$_4$ |
| 15 | azetidin-1-yl | 2 | C$_2$H$_5$ |
| 16 | pyrrol-1-yl | 2 | CF$_3$ |
| 17 | piperidin-1-yl | 2 | C$_6$H$_5$ |
| 18 | pyrrolidin-1-yl | 2 | —(CH$_2$)$_2$CH$_3$ |
| 19 | thiomorpholin-4-yl | 2 | CH$_3$ |
| 20 | thiomorpholin-4-yl | 2 | C$_2$H$_5$ |
| 21 | thiomorpholin-4-yl | 1 | CH$_3$ |
| 22 | thiomorpholin-4-yl | 0 | CH$_3$ |

TABLE IA-continued $$Y-(O)_nS\underset{N}{\overset{}{\bigcirc}}OSO_2R^3$$

| Compound No | Y | n | R³ |
|---|---|---|---|
| 23 | morpholin-N-yl | 1 | CH₃ |
| 24 | morpholin-N-yl | 0 | CH₃ |
| 25 | pyrrol-1-yl | 1 | CH₃ |
| 26 | pyrrol-1-yl | 0 | CH₃ |
| 29 | pyrrolidin-1-yl | 1 | CH₃ |
| 30 | pyrrolidin-1-yl | 0 | CH₃ |
| 31 | piperidin-1-yl | 1 | CH₃ |
| 32 | piperidin-1-yl | 0 | CH₃ |
| 33 | azetidin-1-yl | 1 | CH₃ |
| 34 | azetidin-1-yl | 0 | CH₃ |
| 94 | pyrazol-1-yl | 2 | CH₃ |
| 95 | 1,2,3-triazol-1-yl | 2 | CH₃ |
| 96 | 1,2,4-triazol-1-yl | 2 | CH₃ |
| 97 | 1,2,4-triazol-4-yl | 2 | CH₃ |
| 98 | 2-oxoimidazolidin-1-yl | 2 | CH₃ |
| 99 | 3-methyl-2-oxoimidazolidin-1-yl | 2 | CH₃ |
| 100 | 2-oxo-2,3-dihydropyrimidin-1-yl | 2 | CH₃ |
| 101 | 2-oxopyridin-1-yl | 2 | CH₃ |
| 102 | benzimidazol-1-yl | 2 | CH₃ |

TABLE IB $$\underset{N}{\overset{S(O)_n-Y}{\bigcirc}}OSO_2R^3$$

| Compound No | Y | n | R³ |
|---|---|---|---|
| 35 | morpholin-N-yl | 2 | CH₃ |
| 36 | azetidin-1-yl | 2 | CH₃ |
| 37 | piperidin-1-yl | 2 | CH₃ |

TABLE IB-continued

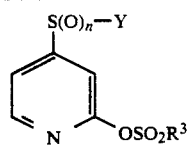

| Compound No | Y | n | R³ |
|---|---|---|---|
| 38 | pyrrole-N— | 2 | CH₃ |
| 39 | pyrrolidine-N— | 2 | CH₃ |
| 40 | imidazole-N— | 2 | CH₃ |
| 41 | 2H-tetrazol-2-yl | 2 | CH₃ |
| 42 | 1H-tetrazol-1-yl | 2 | CH₃ |
| 44 | 2-oxo-oxazolidin-3-yl | 2 | CH₃ |
| 45 | glutarimido-N— | 2 | CH₃ |
| 46 | succinimido-N— | 2 | CH₃ |
| 47 | maleimido-N— | 2 | CH₃ |
| 48 | morpholino-N— | 2 | 4-CH₃-C₆H₄— |
| 49 | azetidin-N— | 2 | C₂H₅ |

TABLE IB-continued

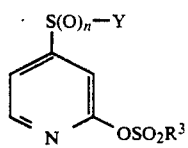

| Compound No | Y | n | R³ |
|---|---|---|---|
| 50 | pyrrole-N— | 2 | CF₃ |
| 51 | piperidino-N— | 2 | C₆H₅ |
| 52 | pyrrolidine-N— | 2 | —(CH₂)₂CH₃ |
| 53 | thiomorpholino-N— | 2 | CH₃ |
| 54 | thiomorpholino-N— | 2 | C₂H₅ |
| 55 | thiomorpholino-N— | 1 | CH₃ |
| 56 | thiomorpholino-N— | 0 | CH₃ |
| 57 | morpholino-N— | 1 | CH₃ |
| 58 | morpholino-N— | 0 | CH₃ |
| 59 | pyrrole-N— | 1 | CH₃ |
| 60 | pyrrole-N— | 0 | CH₃ |
| 63 | pyrrolidine-N— | 1 | CH₃ |

TABLE IB-continued structure: pyridine with S(O)n–Y at 4-position and OSO2R3 at 2-position

| Compound No | Y | n | R³ |
|---|---|---|---|
| 64 | pyrrolidin-1-yl | 0 | CH₃ |
| 65 | piperidin-1-yl | 1 | CH₃ |
| 66 | piperidin-1-yl | 0 | CH₃ |
| 67 | azetidin-1-yl | 1 | CH₃ |
| 68 | azetidin-1-yl | 0 | CH₃ |
| 103 | pyrazol-1-yl | 2 | CH₃ |
| 104 | 1,2,3-triazol-1-yl | 2 | CH₃ |
| 105 | 1,2,4-triazol-1-yl | 2 | CH₃ |
| 106 | 1,2,4-triazol-4-yl | 2 | CH₃ |
| 107 | 2-oxoimidazolidin-1-yl (NH) | 2 | CH₃ |
| 108 | 3-methyl-2-oxoimidazolidin-1-yl | 2 | CH₃ |
| 109 | 2-oxo-2,3-dihydropyrimidin-1-yl | 2 | CH₃ |
| 110 | 2-oxopyridin-1-yl | 2 | CH₃ |
| 111 | benzimidazol-1-yl | 2 | CH₃ |

TABLE 1C structure: benzene with Y–(O)nS– at 3-position and OSO2R3 at 1-position

| Compound No | Y | n | R³ |
|---|---|---|---|
| 69 | morpholin-4-yl | 2 | CH₃ |
| 70 | azetidin-1-yl | 2 | CH₃ |
| 71 | piperidin-1-yl | 2 | CH₃ |
| 72 | 2,5-dihydropyrrol-1-yl | 2 | CH₃ |
| 73 | pyrrolidin-1-yl | 2 | CH₃ |
| 74 | imidazol-1-yl | 2 | CH₃ |
| 75 | 1,2,3-triazol-2-yl | 2 | CH₃ |
| 76 | tetrazol-2-yl | 2 | CH₃ |

TABLE 1C-continued $$Y-(O)_nS-\text{[phenyl]}-OSO_2R^3$$

| Compound No | Y | n | R³ |
|---|---|---|---|
| 78 | oxazolidin-2-on-3-yl | 2 | CH₃ |
| 79 | glutarimid-1-yl | 2 | CH₃ |
| 80 | succinimid-1-yl | 2 | CH₃ |
| 81 | succinimid-1-yl | 2 | CH₃ |
| 82 | morpholin-4-yl | 2 | 4-CH₃-C₆H₄ |
| 83 | azetidin-1-yl | 2 | C₂H₅ |
| 84 | pyrrol-1-yl | 2 | CF₃ |
| 85 | piperidin-1-yl | 2 | C₆H₅ |
| 86 | pyrrolidin-1-yl | 2 | —(CH₂)₂CH₃ |
| 87 | thiomorpholin-4-yl | 2 | CH₃ |
| 88 | thiomorpholin-4-yl | 2 | C₂H₅ |
| 89 | thiomorpholin-4-yl | 1 | CH₃ |
| 90 | thiomorpholin-4-yl | 0 | CH₃ |
| 91 | morpholin-4-yl | 1 | CH₃ |
| 92 | morpholin-4-yl | 0 | CH₃ |
| 93 | pyrrol-1-yl | 1 | CH₃ |
| 94 | pyrrol-1-yl | 0 | CH₃ |
| 97 | pyrrolidin-1-yl | 1 | CH₃ |
| 98 | pyrrolidin-1-yl | 0 | CH₃ |
| 99 | piperidin-1-yl | 1 | CH₃ |
| 100 | piperidin-1-yl | 0 | CH₃ |
| 101 | azetidin-1-yl | 1 | CH₃ |
| 102 | azetidin-1-yl | 0 | CH₃ |
| 112 | pyrazol-1-yl | 2 | CH₃ |

TABLE 1C-continued

Y—(O)ₙS—[phenyl]—OSO₂R³

| Compound No | Y | n | R³ |
|---|---|---|---|
| 113 | (pyrazole/triazole N-) | 2 | CH₃ |
| 114 | (triazole N-) | 2 | CH₃ |
| 115 | (triazole N-) | 2 | CH₃ |
| 116 | (imidazolidinone N-) | 2 | CH₃ |
| 117 | (N-methyl imidazolidinone N-) | 2 | CH₃ |
| 118 | (pyrimidinone N-) | 2 | CH₃ |
| 119 | (2-pyridone N-) | 2 | CH₃ |
| 120 | (benzimidazole N-) | 2 | CH₃ |

Compounds according to this invention fall into different structural types according to the particular nature of the group X in Formula (I) and the position of substitution of the groups R¹ and R2 relative thereto. The selection of an appropriate synthetic process for the preparation of the compounds of the invention is dependent upon the particular structural type which it is desired to prepare. Compounds of formula (I) in which X is nitrogen the groups R¹ and R² occupy the 6 and 2 positions relative thereto may be described by Formula (IA):

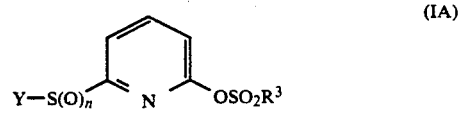

wherein Y, R³ and n have any of the values given hereinbefore. Compounds of formula (I) in which X is nitrogen and the groups R¹ and R² occupy the 4 and 2 positions respectively relative thereto may be described by Formula (IB):

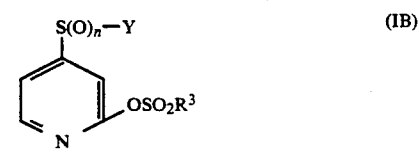

Compounds of formula (I) in which X is carbon bearing a hydrogen atom and the groups R¹ and R² occupy 1 and 3 positions relative to each other may be described by Formula (IC):

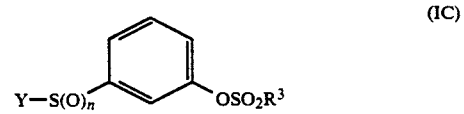

Compounds according to Formulae (IA) and (IB) for which the value of n is 2 may be prepared from the corresponding 2-pyridone precursor of formula (IIA) or (IIB):

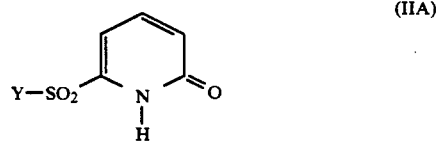

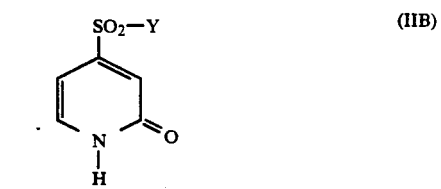

wherein Y has any of the meanings given hereinbefore, by reaction of a sulphonyl halide of formula R³SO₂—Hal, wherein R³ has any of the meanings given hereinbefore and Hal represents halogen, for example chlorine, bromine or fluorine, optionally in the presence of a base, for example pyridine or a trialkylamine such as triethylamine, preferably in an inert solvent such as dichloromethane.

The pyridones of formula (IIA) or (IIB) may be from the corresponding 2-halopyridine of formula IIIA) or (IIIB):

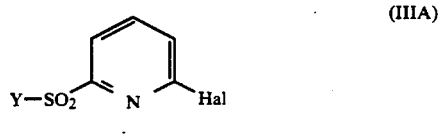

-continued

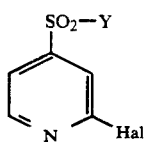 (IIIB)

wherein Y has any of the meanings given hereinbefore and Hal is halogen, for example chlorine, bromine or fluorine, by a two stage process. Firstly the halogen substituent is displaced by a benzyloxy group to give the corresponding 2-benzyloxypyridine of formula (IVA) or (IVB):

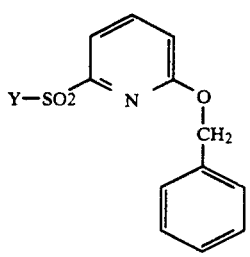 (IVA)

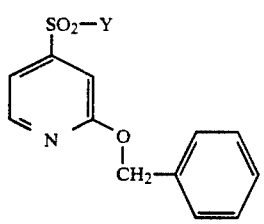 (IVB)

Although an unsubstituted benzyloxy group is favoured for this reaction stage, any benzyl group having a simple ring substituent which is inert to the reaction conditions may also be employed. The displacement may be conveniently performed by reaction with benzyl alcohol in the presence of a base, for example sodium hydride, preferably in an inert solvent such as tetrahydrofuran or dimethylformamide. Debenzylation of the compound of formula (IVA) or (IVB) then gives the corresponding 2-pyridone of formula (IIA) or (IIB). Debenzylation may be conveniently performed under acidic conditions, for example, in the presence of a mixture of acetic acid and concentrated aqueous hydrobromic acid, or in the presence of trifluoroacetic acid in an inert solvent. Debenzylation may also be performed by hydrogenolysis, for example by catalytic hydrogenation.

The 2-pyridones of formula (IIA) and (IIB) may also be prepared from the corresponding 2-halopyridines of formula (IIIA) or (IIIB) directly by acid or base catalysed hydrolysis.

Those skilled in the art will recognise that the 2-pyridones of formula (IIA) and (IIB) exist in tautomeric equilibrium with the corresponding 2-hydroxypyridines.

The compounds of formula (IIIA) and (IIIB) may be prepared from 2,6- and 2,4-dihalopyridines respectively by the following sequence of processes. A 2,6-dihalopyridine, of formula (VA) or a 2,4-dihalopyridine of formula (VB):

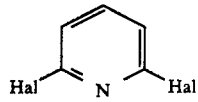 (VA)

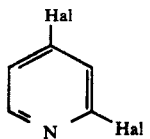 (VB)

wherein Hal represents a halogen, for example chlorine, or fluorine, is reacted with one molar equivalent of benzylthiol or a simple derivative thereof having a ring substituent which is inert to the reaction conditions, in the presence of a base, for example sodium hydride; the reaction may be carried out in any suitable inert solvent such as tetrahydrofuran and produces the corresponding 2-halo-6-benzylthiopyridine or a 2-halo-4-benzylthiopyridine of formula (VIA) or (VIB):

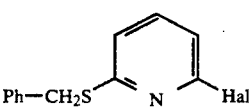 (VIA)

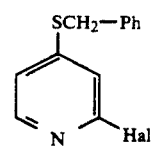 (VIB)

wherein Hal represents a halogen, for example chlorine, bromine or fluorine, and Ph represents phenyl or a simple ring-substituted derivative thereof as described above. The specific 2-halo-4-benzyl substitution pattern of the compounds of formula (VIB) obtained by this process has been confirmed by spectrometric analysis. The compounds of formula (VIA) or (VIB) may then be subjected to oxidative debenzylation, for example by reaction with chlorine in the presence of water optionally in the presence of a solvent, to give the corresponding 2-halopyridine-6-sulphonyl chloride or 2-halopyridine-4-sulphonyl chloride of formula (VIIA) or (VIIB):

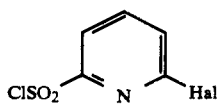 (VIIA)

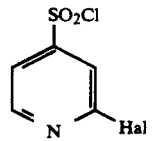 (VIIB)

The compound of formula (VIIA) or (VIIB) may then be reacted either with one equivalent of a compound of Y-H, wherein Y is an optionally substituted heterocyclic ring containing at least one nitrogen atom, the point of attachment of the hydrogen atom being at a ring nitrogen atom, in the presence of an acid scavenger; or with two equivalents of the compound of formula Y-H, to give the desired compound of formula of formula (IIIA) or (IIIB).

These processes are summarised in Schemes I and II for the particular case of the preparation of compounds of formula (IA) wherein n is 2. The summary applies *Mutatis mutandis* for the preparation of compounds of formula (IB).

Scheme I

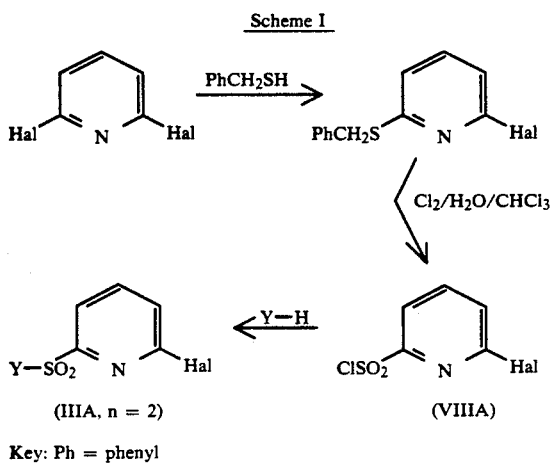

Key: Ph = phenyl

Scheme II

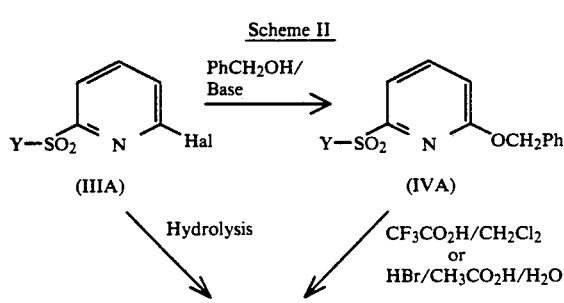

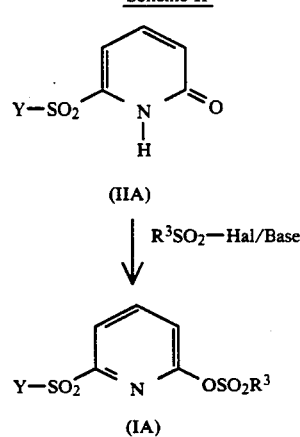

Key: Ph = Phenyl

Specific variations of these processes may be appropriate in certain cases depending on the nature of the group Y. Thus where Y-H represents pyrrole the corresponding compound of formula IVA:

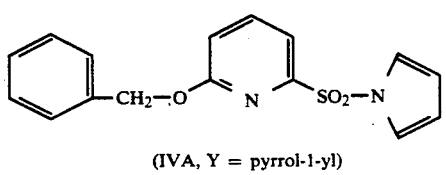

may be prepared by the process described in Scheme III.

Scheme III

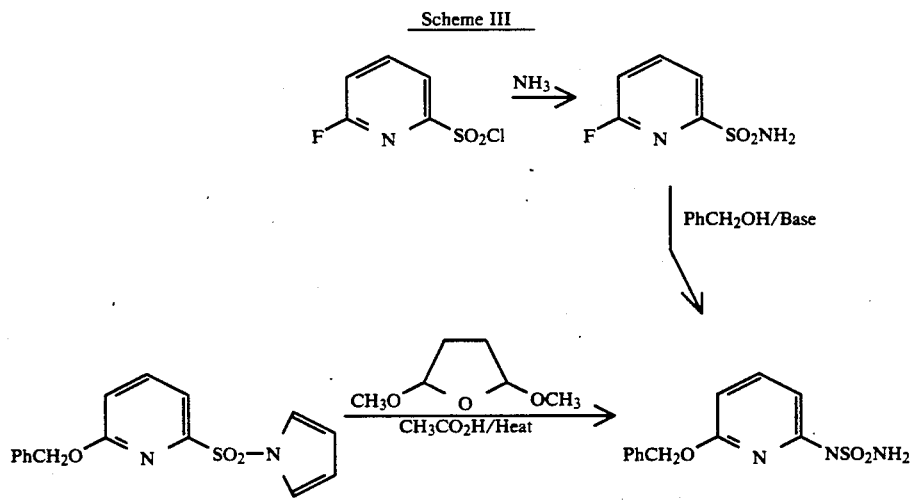

Key: Ph = C$_6$H$_5$

Where Y represents azetidine-1-yl, the corresponding compound of formula IVA:

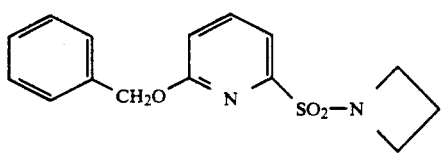

may be prepared by the process described in Scheme IV.

SCHEME IV

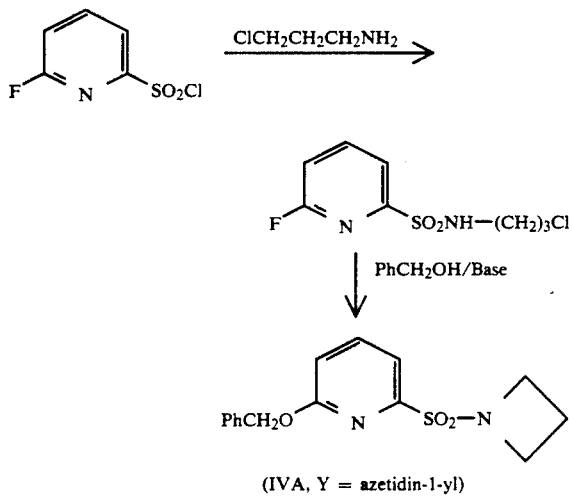

Key: Ph = C₆H₅

Compounds of formula (IA) having a lower oxidation state (i.e. for which the value of n is 0 or 1) may be prepared from 2,6-dihydroxypyridine by the following sequence of processes. The dihydroxypyridine is reacted with two molar equivalents of a sulphonyl halide of formula $R^3SO_2$-Hal, wherein $R^3$ has any of the meanings given hereinbefore and Hal represents halogen, for example chlorine or bromine. The reaction may be carried out in the presence of a base such as pyridine or a trialkylamine for example triethylamine or trimethylamine, in a suitable inert solvent such as dichloromethane, to give the corresponding 2,6-bis sulphonate of formula (VIIIA). Reaction of this product with one molar equivalent of benzenethiol or a simple derivative thereof in the presence of a base in an inert solvent then gives the corresponding compound of formula (IXA):

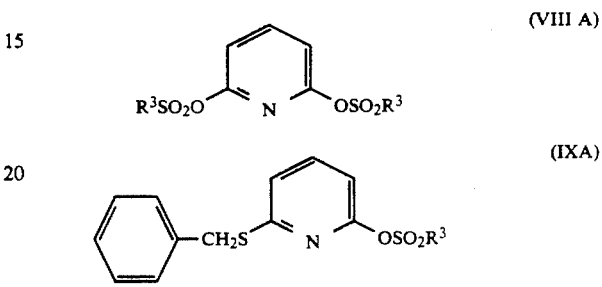

Debenzylation of the compound of formula (IXA) by reaction with sulphuryl chloride in an inert solvent produces an intermediate sulphenyl chloride which may be reacted with a compound of formula Y-H, wherein Y is an optionally substituted heterocyclic ring containing at least one nitrogen atom, the point of attachment of the hydrogen atom being at a ring nitrogen atom, to give the corresponding product of formula (IA) for which n is 0. The corresponding compound of formula (IA) for which n is 1 may be obtained by controlled oxidation of this product, for example by reaction with meta-chloroperbenzoic acid. These processes are summarised in Scheme V.

Scheme V

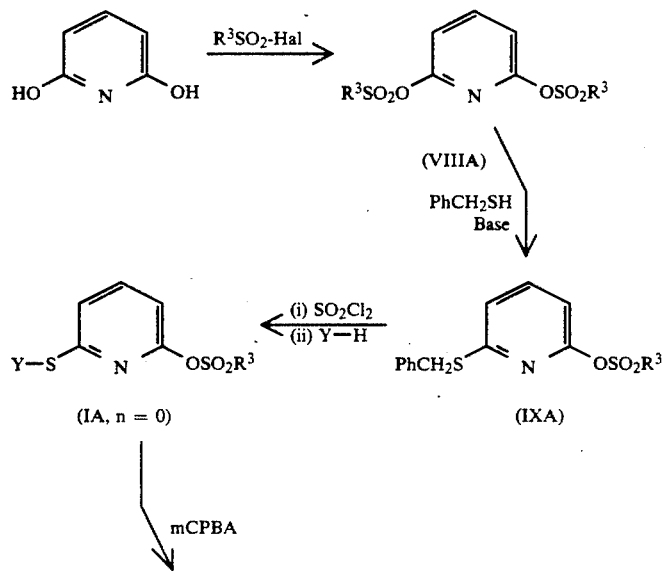

Scheme V

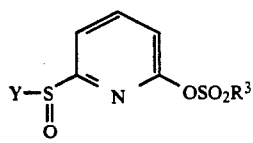

(IA, n = 1)

Key:
Ph = Phenyl
mCPBA = m-chloroperbenzoic acid.

Compounds of formula (IC) wherein Y and $R^3$ have any of the meanings of given hereinbefore and wherein n is 2 may be prepared from 3-benzoyloxybenzenesulphonyl chloride by the following sequence of processes, 3-benzoyloxybenzenesulphonyl chloride may be reacted with a compound of formula Y-H, wherein Y is an optionally substituted heterocyclic ring containing at least one nitrogen atom, the point of attachment of the hydrogen atom being at a ring nitrogen atom, either in the presence of an acid scavenger, for example pyridine or a trialkylamine such as triethylamine, or in the presence of excess of the compound of formula Y-H, to give the corresponding compound of formula (X):

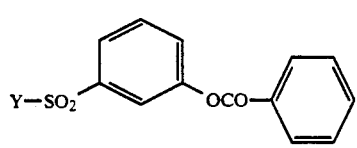

(X)

Basic hydrolysis of the compound of formula (X), for example by reaction with an alkali metal hydroxide such as sodium hydroxide in a suitable solvent such as tetrahydrofuran gives the corresponding 3-hydroxybenzenesulphonamide of formula (XI):

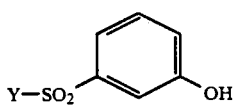

(XI)

which may be reacted with a sulphonyl halide of formula $R^3SO_2$-Hal, wherein $R^3$ has any of the meanings given hereinbefore and Hal is a halogen atom, for example chlorine or bromine, to give the desired compound of formula (IC). These processes are summarised in Scheme VI. The preparation of 3-benzoyloxybenzenesulphonyl chloride is described by Kato et al in The Journal of Pesticide Science, Volume 13, pp 107-115 (1988).

Scheme VI

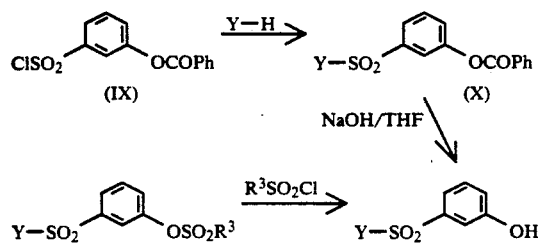

Key: THF = Tetrahydrofuran
Ph = Phenyl

Individual variants of the general processes described herein may be necessary in specific cases where the nature of the substituents may give rise to the possibility of competing reactions. Selection of appropriate variants in such cases falls within the normal skill of the art. By way of example, a specific variant of the processes described, particularly suitable for the preparation of compounds of formula (I) wherein $R^3$ is ethenyl is summarised in Scheme VII. Other variants of the general processes described herein are described in the Examples.

Scheme VII

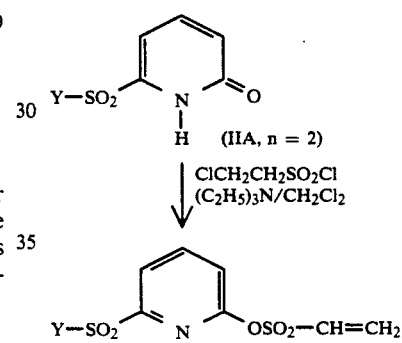

All of the processes described herein may be carried out using alternative solvents or diluents may be accelerated or lead to higher yields of product when performed at elevated temperatures or in the presence of appropriate catalysts. Further details of many of the processes described herein may be found in the Examples. Many of the intermediates described herein are believed to be novel. In a further aspect, therefore, the invention provides the following:

a compound of formula (II):

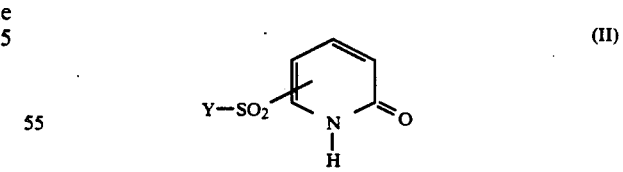

(II)

wherein Y has any of the values given hereinbefore and the group $YSO_2$ is in the 4 or the 6 position relative to the ring nitrogen atom;

a compound of formula (III):

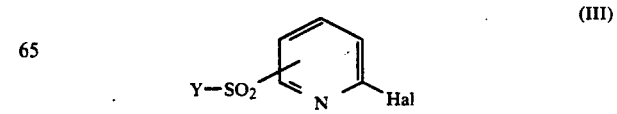

(III)

wherein Hal is a halogen atom, and Y has any of the values given hereinbefore, and the group YSO₂ is in the 4 or the 6 position relative to the ring nitrogen atom;

a compound of formula (IV):

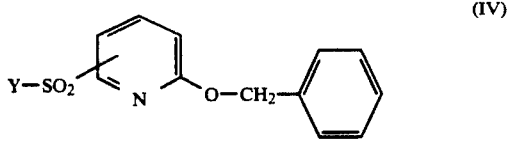

wherein Y has any of the values given hereinbefore and the group YSO₂ is in the 4 or the 6 position relative to the ring nitrogen atom;

a compound of formula (X):

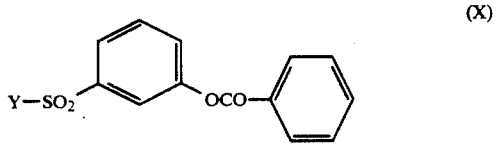

wherein Y has any of the values given hereinbefore; and a compound of formula (XI):

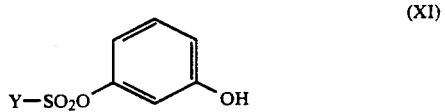

wherein Y has any of the values given hereinbefore.

The compounds of formula (I) may be used to combat and control infestations of insect pests. The insect pests which may be combated and controlled by the use of the invention compounds include those pests associated with agriculture (which term includes the growing of crops for food and fibre products, horticulture and animal husbandry), forestry, the storage of products of vegetable origin, such as fruit grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredient of the composition or they may be admixed with one or more additional active ingredients such as insecticides, insecticide synergists, herbicides, fungicides or plant growth regulators where appropriate.

Suitable additonal active ingredients for inclusion in admixture with the compounds of the invention may be compounds which will broaden the spectrum of activity of the compounds of the invention or increase their persistence in the location of the pest. They may synergise the activity of the compounds of the invention or complement the activity, for example by increasing the speed of effect, improving kill or knockdown of target insect pests, or overcoming repellency. Additionally, multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) natural pyrethrins or pyrethroids such as permethrin, fenvalerate, deltamethrin, cyhalothrin, lambdacyhalothrin, biphenthrin, fenpropathrin, cyfluthrin, tefluthrin, empenthrin, cypermethrin, ethofenprox, tetramethrin, bioallethrin, fenfluthrin, prallethrin, 5-benzyl-3-furylmethyl (E)-(1R,3S)-2,2-dimethyl-3-(2-oxothiolan-3-ylidenemethyl)cyclopropane carboxylate and pentafluorobenzyl (cis)-3-[2-fluoro-2-(methoxycarbonyl)ethenyl]-2,2-dimethylcyclopropane carboxylate;

(b) organophosphates such as profenofos, sulprofos, dichlorvos, methyl parathion, azinphos-methyl, demeton-s-methyl, heptenophos, thiometon, fenamiphos, monocrotophos, triazophos, methamidophos, dimethoate, phosphamidon, malathion, chlorpyrifos, phosalone, fensulphothion, fonofos, phorate, phoxim, pyrimiphos-methyl, fenitrothion and diazinon;

(c) carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) benzoyl ureas such as triflumuron and chlorofluazuron;

(e) organic tin compounds such as cyhexatin, fenbutatin oxide and azocyclotin;

(f) macrolides such as avermectins or milbemycins, for example abamectin, avermectin and milbemycin;

(g) hormones and synthetic mimics thereof such as juvenile hormone, juvabione, ecdysones, methoprene and hydroprene;

(h) pheromones;

(i) organochlorine compounds such as benzene hexachloride, DDT, chlordane, dieldrin and endosulfan In addition to the major chemical classes of insecticide listed above, other insecticides having particular targets may be employed in the mixture if appropriate for the intended utility of the mixture. For instance selective insecticides for particular crops, for example stem borer specific insecticides for use in rice such as cartap or buprofezin, can be employed Alternatively, insecticides or acaricides specific for the control of specific insect growth stages, for example ovolarvicides such as clofentezine, amitraz, chlordimeform, flubenzimine, hexythiazox and tetradifon; motilicides such as dicofol or propargite; adulticides such as bromopropylate, chlorobenzilate; or insect growth regulators such as hydramethylnon, cyromazine, methoprene, chlorfluazuron and diflubenzuron may also be included in the compositions. Examples of suitable insecticide synergists for use in the compositions include piperonyl butoxide, sesamex and dodecyl imidazole.

Suitable herbicides, fungicides and plant growth regulators for inclusion in the compositions will depend upon the intended target and the effect required. An example of a rice-selective herbicide which can be included is propanil; an example of a plant growth regulator for use in cotton is mepiquat; an example of a plant growth regulator for use in rice is paclobutrazol; and examples of fungicides for use in rice include blasticides such as blasticidin-S. The choice of other ingredients to be used in admixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pest to be controlled, and the effects required of the mixture. However, in general, the additional active ingredient of the composition will be applied at about the rate at which it would be applied on its own, or at a lower rate if synergy occurs.

The compositions may be in the form of dusting powders wherein the active ingredient is mixed with a solid diluent or carrier, for example kaolin, bentonite, kieselguhr or talc, or they may be in the form of granules wherein the active ingredient is absorbed in a porous granular material, for example pumice or another inorganic carrier. Granule compositions intended for use in aquatic locations such as paddy fields and ponds may optionally incorporate an inert, non-volatile solvent of specific gravity less than 1.0, facilitating the release of the active ingredient in solution in the solvent at the water surface following breakdown of the granule.

Alternatively, the compositions may be in the form of liquid preparations to be used as dips, sprays or aerosols. Dips and sprays are generally aqueous dispersions or emulsions of the active ingredient in the presence of one or more known wetting agents (surface active agents). Aerosol compositions may contain the active ingredient or ingredients, a propellant and an inert diluent, for example odourless kerosene or alkylated benzenes. In a preferred form, aerosol compositions may contain from 0.005% to 4% of active ingredient or ingredients, the remainder of the composition comprising a solvent, selected from odourless kerosene and alkylated benzenes, and a propellant. Aerosol compositions may optionally incorporate other additives, for example perfumes or corrosion inhibitors.

Wetting agents, dispersing agents and emulsifying agents may be of the cationic, anionic or non-ionic type. Suitable agents of the cationic type include, for example, quaternary ammonium compounds, for example cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium lignosulphonate, calcium lignosulphonate, ammonium lignosulphonate, butylnaphthalenesulphonate and a mixture of the sodium salts of diisopropyl- and triisopropyl naphthalenesulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a sutiable solvent, for example a ketonic solvent such as diacetone alcohol, or an aromatic solvent such as trimethylbenzene, and optionally adding the mixture so obtained to water which may contain one or more known wetting, dispersing or emulsifying agents. Other suitable organic solvents are dimethylformamide, ethylene dichloride, isopropyl alcohol, propylene glycol and other glycols, diacetone alcohol, toluene, kerosene, white oil, methylnaphthalene, xylenes, trichloroethylene, N-methyl-2-pyrollidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and, after such storage, to be capable of dilution with water to form aqueous preparations which remain homogeneous for a sufficient time to enable them to be applied by conventional spray equipment. The concentrates may contain 1-99% by weight of the active ingredient or ingredients. When diluted to form aqueous preparations, such preparations may contain varying amounts of the active ingredient depending upon the purpose for which they are to be used. For agricultural or horticultural purposes, an aqueous preparation containing between 0.0001% and 0.1% by weight of the active ingredient or ingredients is particularly useful. In use, the compositions are applied to the pests, to the locus of the pests, to the habitat of the pests, or to growing plants liable to infestation by the pests, by any of the known means of applying pesticidal compositions, for example by dusting or spraying or in a granular formulation. The compounds of formula (I) and compositions comprising them are very toxic to a variety of insect, and other invertebrate pests, including, for example, the following:

*Myzus persicae* (aphid)
*Aphis gossypii* (aphid)
*Aphis fabae* (aphid)
*Megoura viceae* (aphid)
*Plutella maculipennis* (diamond back moth)
*Spodoptera littoralis* (cotton leafworm)
*Heliothis virescens* (tobacco budworm)
*Diabrotica spp.* (rootworms)
*Agrotis spp.* (cutworms)
*Chilo partellus* (maize stem borer)
*Nilaparvata lugens* (planthopper)
*Nephotettix cincticeps* (leafhopper)
*Lissorhoptrus oryzophilus* (rice water weevil)

The compounds of formula (I) are particularly useful for the control pests of hopper pests such as planthoppers (Delphacidae), for example Nilaparvata spp. leafhoppers (Cicadellidae), for example Nephotettix spp., and *Lissorhoptrus oryzophilus* (rice water weevil). They are also effective against soil pests such as Diabrotica spp. and sucking pests such as aphids, for example Myzus spp., Aphis spp. or Megoura spp. The compounds are characterised by a particularly high level of systemic activity.

The following Examples illustrate various aspects of this invention. In the preparation Examples the products were usually identified and characterised by means of nuclear magnetic resonance (NMR) spectroscopy and infra red (IR) spectroscopy. In each case where a product is specifically named its spectral characteristics are consistent with the assigned structure. In the Examples, gas liquid chromatography (GLC) retention times were determined on a Hewlett Packard 5890 Gas Chromatograph, using a Chrompak C.P. Sil 5 C.B. column of 12.5 m length and 0.2 mm internal diameter. Unless otherwise stated, the injection temperature was 100° C., and a temperature gradient of 15° C. per minute employed, up to a maximum temperature of 280° C., maintained for 4 minutes. The carrier gas was helium at a column head pressure maintained at 11 psi. Alternative injection and maximum temperatures are indicated in the Examples where appropriate.

$^1$H NMR spectrometry was performed at a frequency of 270 MHz on a Jeol FX 270 NMR spectrometry unless otherwise indicated. 90 Mhz, 60 Mhz and 400 MHz $^1$H NMR spectrometry were performed using Jeol FX 90Q, Jeol PMX 60 SI and Jeol GX 400 spectrometers. $^{19}$F NMR spectrometry was performed using a Jeol FX 90Q spectrometer at a frequency of 84.26 MHz. All NMR shift values (δ) are quoted in ppm relative to a standard (TMS or CFCl$_3$) In the NMR data, the following abbreviations are used: s=singlet, d=doublet, t=triplet, q=quartet, dd=double doublet, m=multiplet, b=broad. Molecular ion (M+) peaks were determined on one of three mass spectrometers: Jeol DX 303, Kratos MS 80 or Hewlett Packard HP 5992.

EXAMPLE 1

This Example illustrates the stages in the preparation of 2-(morpholine-4-sulphonyl)-6-(methanesulphonyloxy)pyridine (compound No. 1)

(i) 2-benzylthio-6-fluoropyridine

A solution of benzylthiol (5.4 g) in tetrahydrofuran (25 cm$^3$) was added dropwise to a stirred suspension of sodium hydride (1.9 g of a 55% of a dispersion in oil) in tetrahydrofuran (350 cm$^3$) under a nitrogen atmosphere. The mixture was stirred for 30 minutes and a solution of 2,6-difluoropyridine (5 g) in tetrahydrofuran (25 cm$^3$) was added dropwise. The mixture was stirred for a further 3 hours and then carefully quenched with water. The products were extracted into diethyl ether and the combined ether extracts were washed with water and brine solution, then dried over anhydrous magnesium sulphate, filtered and concentrated by evaporation under reduced pressure. The residual dark liquid was purified by chromatography on a silica gel support, eluting with hexane containing 5% by volume ethyl acetate. Fractions containing 15–20 cm$^3$ of eluent were collected separately during the elution, the product being collected in fractions 11 to 19. Evaporation of the eluent gave the title product (7.1 g) as a clear liquid.

$^1$H NMR (CDCl$_3$): 4.40 (2H,s); 6.57 (1H,dd); 7.02 (1H,dd); 7.2–7.6 (6H,m).

(ii) 6-fluoropyridine-2-sulphonyl chloride

Chlorine gas was bubbled through a vigorously stirred mixture of chloroform (20 cm$^3$), water (20 cm$^3$) and 2-benzylthio-6-fluoropyridine (1 g) for a total of 95 minutes. Aqueous sodium metabisulphite solution was added to the mixture and the chloroform layer was separated. The aqueous layer was extracted with further chloroform and the combined chloroform layers were washed with water, dried over anhydrous magnesium sulphate, filtered and concentrated by evaporation under reduced pressure to yield a residual oil (2.0 g) which was used without further purification.

(iii) 2-(morpholine-4-sulphonyl)-6-fluoropyridine

To a solution of 6-fluoropyridine-2-sulphonyl chloride (1.96 g) in chloroform (40 cm$^3$) at 0° C. was added a solution of morpholine (1.74 g) in chloroform (20 cm$^3$). The reaction was quenched in water (100 cm$^3$) and the product extracted into chloroform (3×50 cm$^3$). The combined organic layers were washed with water, dried over anhydrous magnesium sulphate and the solvent evaporated under reduced pressure to give the title compound which was used without further purification.

$^1$H NMR (CDCl$_3$) 3.37(4H,m); 3.75(4H,m); 7.18 (1H,dd); 7.85(1H,m); 8.05(1H,m).

(iv) 2-(morpholine-4-sulphonyl)-6-benzyloxypyridine

To a solution of 2-(morpholine-4-sulphonyl)-6-fluoropyridine (2.46 g) in dimethyl formamide (40 cm$^3$), at 0° C. under an atmosphere of nitrogen was added a solution of sodium benzylate (22 m moles) in dimethyl formamide (20 cm$^3$). The reaction mixture was added to water (100 cm$^3$) and the product extracted into ethyl acetate (4×30 cm$^3$). The combined organic washings were washed with water and brine, then dried over anhydrous magnesium sulphate. The solvent was evaporated under reduced pressure and the crude product purified by silica chromatography eluting with 30% ethyl acetate in hexane.

$^1$H NMR (CDCl$_3$): 3.20(4H,m); 3.70(4H,m); 5.41(2H,s); 7.05(1H,d); 7.40(5H,m); 7.55(1H,d); 7.80(1H,m).

(v) 2-(morpholine-4-sulphonyl)pyrid-6-one

To a solution of 2-(morpholine-4-sulphonyl)-6-benzyloxypyridine (0.6 g) in acetic acid (10 cm$^3$) was added 48% hydrobromic acid (10 cm$^3$). The mixture was heated to 45° C., then stirred until the reaction was complete. The mixture was cooled, quenched in water (50 cm$^3$) and the product extracted into ethyl acetate (4×20 cm$^3$). The combined organic layers were washed with water, dried over anhydrous magnesium sulphate and the solvent evaporated under reduced pressure. The crude product was purified by silica chromatography eluting with hexane containing a gradually increased proportion of ethyl acetate (from 50%–60%).

$^1$H NMR (CDCl$_3$): 3.25 (4H,m); 3.77 (4H,m); 6.90 (1H,d); 7.15 (1H,d); 7.69 (1H,dd).

(vi) 2-(morpholine-4-sulphonyl)-6-(methanesulphonyloxy) pyridine (Compound No. 1)

A solution of the pyridone prepared in stage (v) (0.27 g) in dichoromethane (30 cm$^3$) under nitrogen was cooled to 0° C. and a solution of mesyl chloride in chloroform was added (0.12 g in 5 cm$^3$). The reaction mixture was stirred for 5 minutes then treated with triethylamine (0.1 g) in dichloromethane.

After the completion of the reaction the reaction mixture was quenched into water (100 cm$^3$) and the product extracted into dichloromethane. The combined organic layers were washed with water, dried over andhydrous magnesium sulphate and the solvent evaporated under reduced pressure. The crude product was purified by silica chromatography, eluting with 50% ethyl acetate in hexane to give the title product (0.27 g).

Melting Point 113°–114° C.

$^1$H NMR (CDCl$_3$): 3.29 (4H, m); 3.58 (3H,s); 3.75 (4H,m); 7.30 (1H,d); 7.90 (1H,d); 8.07 (1H,t).

Examples 2–6 illustrate the preparation of further examples according to the invention using essentially the same procedures as those described in stages (i)–(vi) of Example 1. In each example, characteristic data are given for the final products and intermediates which have not been described in earlier examples. In some cases, intermediates may not have been isolated or purified, and no data are recorded. Individual reaction conditions may have differed from those described in Example 1 according to requirements for optimisation using techniques within the normal skill of the chemist. Intermediates are identified by name and reaction stage number [(i)–(vi)].

EXAMPLE 2

(iii) 2-(piperidine-1-sulphonyl)-6-fluoropyridine $^1$H NMR (CDCl$_3$): 1.4–1.75 (6H,m); 3.30 (4H,m); 7.12 (1H,dd); 7.82 (1H,dd); 8.00 (1H,m).

(v) 2-(piperidine-1-sulphonyl)pyrid-6-one $^1$H NMR (CDCl$_3$): 1.5–1.7 (6H,m); 3.20 (4H,m); 6.85 (1H,d); 6.95 (1H,d); 7.60 (1H,dd).

(vi) 2-(piperidine-1-sulphonyl)-6-(methanesulphonyloxy)pyridine (Compound No.3)

$^1$H NMR (CDCl$_3$): 1.5 (2H,m); 1.6–1.7 (4H,m); 3.28 (4H,m); 3.58 (3H,s); 7.27 (1H,d); 7.90 (1H,d); 8.05 (1H,t).

EXAMPLE 3

(iii) 2-(thiomorpholine-4-sulphonyl)-6-fluoropyridine $^1$H NMR (CDCl$_3$): 2.70 (4H,m); 3.65 (4H,m); 7.17 (1H,dd); 7.83 (1H,dd); 8.00 (1H,m).

(v) 2-(thiomorpholine-4-sulphonyl)pyrid-6-one $^1$H NMR (CDCl$_3$): 2.70 (4H,m); 3.55 (4H,m); 6.89 (1H,d); 7.10 (1H,d); 7.65 (1H,m).

(vi) 2-(thiomorpholine-4-sulphonyl)-6-(methanesulphonyloxy)pyridine. (Compound No. 19).

$^1$H NMR (CDCl$_3$): 2.70 (4H,m); 3.55 (3H,s); 3.60 (4H,m); 7.30 (1H,d); 7.89 (1H,d); 8.05 (1H,t).

EXAMPLE 4

(iii) 2-(pyrrolidine-1-sulphonyl)-6-fluoropyridine $^1$H NMR (CDCl$_3$): 1.80 (4H,m); 3.50 (4H,m); 7.14 (1H,dd); 7.86 (1H,dd); 8.02 (1H,dd).

(v) 2-(pyrrolidine-1-sulphonyl)pyrid-6-one $^1$H NMR (CDCl$_3$): 1.88 (4H,m); 3.40 (4H,m); 6.84 (1H,d); 7.00 (1H,d); 7.60 (1H,dd).

(vi) 2-(pyrrolidine-1-sulphonyl)-6-(methanesulphonyloxy)pyridine (Compound No. 5)

$^1$H NMR (CDCl$_3$); 1.83 (4H,m); 3.45 (4H,m); 3.57 (3H, s); 7.27 (1H,d); 7.90 (1H,d); 8.03 (1H,t).

EXAMPLE 5

(iii) 2-[N-(3-chloropropyl)sulphamoyl]-6-fluoropyridine prepared according to the method of Example 1 (iii) using 3-chloropropylamine in place of morpholine $^1$H NMR (CDCl$_3$): 2.01 (2H,m); 3.30 (2H,m); 3.64 (2H,m); 5.10 (1H,broad t); 7.18 (1H,dd); 7.90 (1H,dd); 8.05 (1H,m).

(iv) 2-(azetidine-1-sulphonyl)-6-benzyloxypyridine

A solution of sodium benzylate (72.0 mmoles) in dimethyl formamide (20 cm$^3$) was added to a solution of 2-[N-(3-chloropropyl)sulphamoyl]-6-fluoropyridine (1.55 g) in dimethyl formamide (40 cm$^3$) under nitrogen at a temperature of 0° C.

The reaction mixture was quenched in water (100 cm$^3$) and the product extracted into ethyl acetate (4×30 cm$^3$). The combined organic layers were washed with water and brine and dried over anhydrous magnesium sulphate. The solvent was evaporated under reduced pressure and the ring-closed product purified by silica chromatography eluting with 30% ethyl acetate in hexane.

$^1$H NMR (CDCl$_3$): 2.02 (2H,m); 4.00 (4H,m); 5.48 (2H,s); 7.04 (1H,d); 7.35 (5H,m); 7.58 (1H,d); 7.80 (1H,t).

(v) 2-(azetidine-1-sulphonyl)pyrid-6-one $^1$H NMR (CDCl$_3$): 2.20 (2H,m); 4.00 (4H,t); 6.92 (1H,d); 7.10 (1H,d); 7.69 (1H,dd).

(vi) 2-(azetidine-1-sulphonyl)-6-(methanesulphonyloxy)pyridine (Compound No. 2)

$^1$H NMR (CDCl$_3$): 2.20 (2H,m); 3.60 (3H,s); 4.10 (4H,t); 7.33 (1H,d); 7.95 (1H,d); 8.05 (1H,t).

EXAMPLE 6

This Example illustrates the stages in the preparation of 2-(pyrrole-1-sulphonyl)-6-(methanesulphonyloxy)pyridine (i) 6-fluoro-2-sulphamoylpyridine A solution of 6-fluoropyridine-2-sulphonyl chloride (1.2 g) in diethyl ether (100 cm$^3$) was cooled to −60° C. and ammonia was slowly bubbled through the stirred solution. Further 6 fluoropyridine-2-sulphonyl chloride (1 g) was added and the introduction of ammonia continued. The reaction mixture was warmed to the ambient temperature and poured into water, and the product extracted into diethyl ether. The aqueous layer was neutralised with dilute aqueous hydrochloric acid solution and then further extracted with diethyl ether. The combined diethyl ether washings were dried over anhydrous magnesium sulphate, filtered and evaporated to leave the title product.

$^1$H NMR (DMSO): 7.02 (2H,bs); 7.18 (1H,dd); 7.90 (1H,dd); 8.09 (1H,dd).

(ii) 6-benzyloxy-2-sulphamoylpyridine

This compound was prepared using the method of Example 1 (iv)

$^1$H NMR (CDCl$_3$): 4.80 (2H,bs); 5.40 (2H,s); 7.00 (1H,d); 7.40 (5H,m); 7.60 (1H,d); 7.75 (1H,dd).

(iii) 2-(pyrrole-1-sulphonyl)pyrid-6-one

To a stirred solution of 2-sulphamoyl-6-(benzyloxy)pyridine (1 g) in acetic acid (10 cm$^3$) was added 2,5-dimethoxytetrahydrofuran (0.55 g) and the resulting mixture heated to 100° C. for 7 hours. The reaction mixture was added to water (50 cm$^3$) and the product extracted into ethyl acetate (3×20 cm$^3$).

The organic washings were combined, dried over anhydrous magnesium sulphate and the solvent evaporated under reduced pressure to give a crude product identified as 2-(pyrrole-1-sulphonyl)-6-benzyloxypyridine. The crude product was treated with dichloromethane (5 cm$^3$) and trifluoroacetic acid (5 cm$^3$) for 24 hours at the ambient temperature. Toluene (10 cm$^3$) was added and the reaction mixture evaporated to dryness under reduced pressure. The crude product was purified by silica chromatography eluting with 30% ethyl acetate in hexane.

$^1$H NMR (CDCl$_3$): 6.30 (2H,m); 6.95 (1H,d); 7.19 (2H,m); 7.50 (1H,d); 7.79 (1H,t).

(iv) 2-(pyrrole-1-sulphonyl)-6-(methanesulphonyloxy)pyridine (Compound No. 4)

To a stirred solution of 2-(pyrrole-1-sulphonyl)pyrid-6-one (0.22 g) in dichloromethane (20 cm$^3$) under nitrogen at 0° C. was added in solution of mesyl chloride (0.124 g) in dichloromethane (5 cm$^3$) and triethylamine (0.109 g).

The reaction mixture was quenched in water (50 cm$^3$) and the product extracted into dichloromethane (3×15 cm$^3$). The combined organic washings were washed with water, dried over anhydrous magnesium sulphate and the solvent evaporated under reduced pressure.

The crude product was recrystallised from ethyl acetate/hexane.

$^1$H NMR (CDCl$_3$) 3.42 (3H,s); 6.38 (2H,m); 7.20 (2H,m); 7.32 (1H,d); 8.05 (2H,m).

EXAMPLE 7

This Example illustrates an emulsifiable concentrate composition which is readily convertible by dilution with water into a liquid preparation suitable for spraying purposes. The concentrate has the following composition:

|  | % Weight |
| --- | --- |
| Compound 1 | 25.0 |
| SYNPERONIC NP13 (nonylphenol-ethyleneoxide condensate; Synperonic is a registered trade mark). | 2.5 |
| Calcium dodecylbenzenesulphonate | 2.5 |
| AROMASOL H (alkylbenzene solvent; Aromasol is a registered trade mark). | 70 |

EXAMPLE 8

This Example illustrates an emulsifiable concentrate composition which is readily convertible by dilution with water into a liquid preparation suitable for spraying purposes. The concentrate has the following composition:

|  | % Weight |
| --- | --- |
| Compound No 2 | 50.0 |
| SYNPERONIC NP13 (nonylphenol-ethyleneoxide condensate; Synperonic is a registered trade mark). | 6.0 |
| Calcium dodecylbenzenesulphonate | 4.0 |
| AROMASOL H (alkylbenzene solvent; Aromasol is a registered trade mark). | 40.0 |

EXAMPLE 9

This Example illustrates an emulsifiable concentrate composition which is readily convertible by dilution with water into a liquid preparation suitable for spraying purposes. The concentrate has the following composition:

|  | % Weight |
| --- | --- |
| Compound No 3 | 1.0 |
| SYNPERONIC OP10 (octylphenol-ethyleneoxide condensate; Synperonic is a registered trade mark). | 3.0 |
| Calcium dodecylbenzenesulphonate | 2.0 |
| AROMASOL H (alkylbenzene solvent; Aromasol is a registered trade mark). | 94.0 |

EXAMPLE 10

This Example illustrates a wettable powder composition which is readily convertible by dilution with water into a liquid preparation suitable for spraying purposes. The wettable powder has the following composition:

|  | % Weight |
| --- | --- |
| Compound No 4 | 25.0 |
| Silica | 25.0 |
| Sodium lignosulphonate | 5.0 |
| Sodium lauryl sulphate | 2.0 |
| Kaolinite | 43.0 |

EXAMPLE 11

This Example illustrates a wettable powder composition which is readily convertible by dilution with water into a liquid preparation suitable for spraying purposes. The wettable powder has the following composition:

|  | % Weight |
| --- | --- |
| Compound No 5 | 1.0 |
| Sodium lignosulphonate | 5.0 |
| Sodium lauryl sulphate | 2.0 |
| Kaolinite | 92.0 |

EXAMPLE 12

This Example illustrates a wettable powder composition which is readily convertible by dilution with water into a liquid preparation suitable for spraying purposes. The wettable powder has the following composition:

|  | % Weight |
| --- | --- |
| Compound No 19 | 40.0 |
| Silica | 40.0 |
| Calcium lignosulphonate | 5.0 |
| Sodium lauryl sulphate | 2.0 |
| Kaolinite | 13.0 |

EXAMPLE 13

This Example illustrates a dusting powder which may be applied directly to plants or other surfaces and comprises 1% by weight of Compound 19 and 99% by weight of talc.

EXAMPLE 14

This Example illustrates a concentrated liquid formulation suitable for application by ultra low volume techniques after mixing with paraffinic diluents.

|  | % Weight |
| --- | --- |
| Compound No 4 | 90.0 |
| SOLVESSO 200 (inert diluent; Solvesso is a registered trade mark). | 10.0 |

EXAMPLE 15

This Example illustrates a concentrated liquid formulation suitable for application by ultra low volume techniques after mixing with paraffinic diluents.

|  | % Weight |
|---|---|
| Compound No 1 | 25.0 |
| SOLVESSO 200 (inert diluent; Solvesso is a registered trade mark) | 75.0 |

EXAMPLE 16

This Example illustrates a concentrated liquid formulation suitable for application by ultra low volume techniques after mixing with paraffinic diluents.

|  | % Weight |
|---|---|
| Compound No 2 | 10.0 |
| SOLVESSO 200 (inert diluent; Solvesso is a registered trade mark) | 90.0 |

EXAMPLE 17

This Example illustrates a capsule suspension concentrate which is readily convertible by dilution with water to form a preparation suitable for application as an aqueous spray.

|  | % Weight |
|---|---|
| Compound No 1 | 10.0 |
| solvent (e.g. AROMASOL H) | 5.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL; Keltrol is a registered trade mark) | 0.1 |
| Water | 76.4 |

EXAMPLE 18

This Example illustrates a capsule suspension concentrate which is readily convertible by dilution with water to form a preparation suitable for application as an aqueous spray.

|  | % Weight |
|---|---|
| Compound No 5 | 1.0 |
| Alkylbenzene solvent (e.g. AROMASOL H) | 10.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL; Keltrol is a registered trade mark) | 0.1 |
| Water | 80.4 |

EXAMPLE 19

A ready for use granular formulation:

|  | % Weight |
|---|---|
| Compound No 4 | 0.5 |
| SOLVESSO 200 | 0.2 |
| nonylphenol ethoxylate (eg Synperonic NP8) | 0.1 |
| Calcium carbonate granules (0.3–0.7 mm) | 99.2 |

EXAMPLE 20

An aqueous suspension concentrate:

|  | % Weight |
|---|---|
| Compound No 19 | 5.0 |
| Kaolinite | 15.0 |
| Sodium lignosulphonate | 3.0 |
| nonylphenolethoxylate (eg Synperonic NP 8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 63.3 |

EXAMPLE 21

A ready for use dust (D.P.) made from a concentrate

|  | % Weight |
|---|---|
| Concentrate: | |
| Compound No 2 | 10 |
| Silica | 20 |
| Magnesium Carbonate | 70 |
| Dust Example containing 1% active ingredient: | |
| Above concentrate | 10 |
| Talc | 90 |

EXAMPLE 22

This Example illustrates a liquid formulation suitable for direct application by ultra low volume techniques.

|  | % Weight |
|---|---|
| Compound No 3 | 15.0 |
| Cotton seed oil | 50.0 |
| SOLVESSO 200 (inert diluent; SOLVESSO is a registered trade mark) | 35.0 |

EXAMPLE 23

This Example illustrates a ready for use granule formulation.

|  | % Weight |
|---|---|
| Compound No. 1 | 5.0 |
| SYNPERONIC NP8 (nonylphenol-ethyleneoxide condensate; SYNPERONIC is a registered trade mark) | 2.0 |
| Pumice granules (20/40 BS Mesh) | 93.0 |

EXAMPLE 24

This Example illustrates a water dispersible granule formulation

|  | % Weight |
|---|---|
| Compound No. 1 | 5.0 |

-continued

| | % Weight |
|---|---|
| Sodium lignosulphonate | 5.0 |
| Sodium dioctylsulphosuccinate | 5.0 |
| Sodium acetate | 10.0 |
| Montmorillonite powder | 65.0 |

EXAMPLE 25

This Example illustrates a soluble granule formulation suitable for paddy field application containing a non-volatile, low specific gravity solvent.

| | % Weight |
|---|---|
| Compound No. 1 | 1.5 |
| Oleyl alcohol | 12.0 |
| Sodium lignosulphonate | 5.0 |
| Montmorillonite clay | 10.0 |
| Sodium sesquicarbonate | 71.5 |

EXAMPLE 26

This Example illustrates the insecticidal properties of the products of this invention.

The activity of the product was determined using a variety of insect pests. The product were used in the form of liquid preparations containing 500, 250 or 100 parts per million (ppm) by weight of the product. The preparations were made by dissolving the product in acetone and diluting the solutions to give the required concentration of product using as a diluent water containing 0.01% by weight of a nonylphenol ethoxylate wetting agent sold under the trade name SYNPERONIC NX (registered trade mark).

The test procedure adopted with regard to each pest was essentially the same and comprised supporting a number of the pests on a medium which was usually a host plant or a foodstuff on which the pests feed, and treating either or both of the pests and the medium with the preparations. The mortality of the insects was then assessed at periods varying from 1 to 6 days after the treatment (DAT).

The results of the tests are given in Table III for each of the products, at the rate of application indicated (in ppm) in the second column of the Table, as a grading of observed mortality designated as A, B or C, wherein A indicates 80-100% mortality, B indicates 50-79% mortality, and C indicates less than 50% mortality.

In Table III, the test type is designated by a letter code, and the species, support medium, type and duration of the test are given for each code in Table II.

TABLE II

| CODE LETTERS | TEST SPECIES | SUPPORT MEDIUM/FOOD | TYPE OF TEST | DURATION (DAYS) |
|---|---|---|---|---|
| MP | Myzus persicae (aphids) | French bean leaf | Contact | 3 |
| NC | Nephotettix cincticeps | Rice plant | Contact | 2 |
| (2 DAT) | (green leafhopper-nymphs) | | | |
| (6 DAT) | (green leafhopper-nymphs) | " | " | 6 |
| HV | Heliothis virescens | Cotton leaf | Residual | 2 |
| (2 DAT) | (tobacco budworm-larvae) | | | |
| (6 DAT) | (tobacco budworm-larvae) | " | " | 6 |
| SP | Spodoptera exigua | Cotton leaf | " | 2 |
| (2 DAT) | (lesser army worm-larvae) | | | |
| (6 DAT) | (lesser army worm-larvae) | " | " | 6 |
| DB | Diabrotica balteata (rootworm-larvae) | Filter paper/maize seed | " | 2 |

"Contact" indicates a test in which both the medium and the pests were treated. "Residual" indicates a test in which the medium was treated prior to infestation the pests.
DAT: Days after treatment

TABLE III

| Compound No. | Rate (ppm) | MP | NC 2 DAT | NC 6 DAT | HV 2 DAT | HV 6 DAT | SP 2 DAT | SP 6 DAT | DB |
|---|---|---|---|---|---|---|---|---|---|
| 1 | 500 | C | A | — | B | A | C | C | A |
| 2 | 500 | C | A | — | B | A | C | C | A |
| 3 | 500 | C | A | — | C | C | C | C | A |
| 4 | 500 | C | A | — | C | A | C | C | A |
| 5 | 500 | C | A | — | C | B | C | C | A |
| 19 | 500 | C | A | — | C | C | C | C | C |

We claim:

1. A compound of formula:

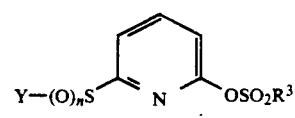

(I)

wherein Y is a 4- 5- or 6- membered heterocyclic ring containing one nitrogen atom at the point of attachment, and, optionally, one other heterocyclic atom selected from the group consisting of oxygen or sulphur and n is 0, 1 or 2; and wherein $R^3$ is $C_{1-8}$ alkyl, $C_{1-4}$ alkyl substituted by a phenyl, $C_{1-8}$ haloalkyl, $C_{2-6}$ alkenyl, $C_{2-4}$ alkenyl substituted by a phenyl, $C_{2-4}$ alkynyl, $C_{2-5}$ alkynyl substituted by phenyl, aryl, $C_{1-4}$ alkyl substituted by a substituted phenyl, $C_{2-4}$ alkynyl substituted by a substituted phenyl, $C_{2-4}$ alkenyl substituted by a substituted phenyl, substituted aryl, wherein the the phenyl or aryl is substituted with alkyl; alkenyl; alkynyl; haloalkyl; halo; or alkoxy, and a group of formula —$N(R^4)(R^5)$ wherein $R^4$ and $R^5$ are independently hydrogen and $C_{1-6}$ alkyl or wherein $R^4$ and $R^5$ together represent —$(CH_2)_p$— wherein p is 2, 3, 4 or 5.

2. A compound as claimed in claim 1 wherein the group Y is either
   (a) a heterocycle or a substituted heterocycle containing one nitrogen atom at the point of attachment, selected from the group consisting of piperidin-1-yl, pyrrolidin-1-yl, pyrrol-1-yl, 3-pyrrolin-1-yl, azetidin-1-yl, aziridin-1-yl, pyrrolidin-2,4-dione-1-yl, 3-pyrrolin-2,4-dione-1-yl, and piperidin-2,6-dione-1-yl, or
   (b) a heterocycle or a substituted heterocycle containing one nitrogen atom at the point of attachment and one oxygen or sulphur atom selected from the group consisting of morpholin-4-yl and thiomorpholin-4-yl.

3. A compound as claimed in claim 1 wherein the group $R^3$ is $C_{1-4}$ alkyl, $C_{1-2}$ alkyl substituted with phenyl, $C_{1-6}$ haloalkyl, $C_{2-4}$ alkenyl, ethenyl, ethenyl substituted with a phenyl, phenyl, pyridyl, 2-thienyl, 3-thienyl, $C_{1-2}$ alkyl substituted with a substituted phenyl, ethenyl substituted with a substituted phenyl, substituted pyridyl wherein the substituents on the substituted phenyl and substituted pyridyl are alkyl; alkenyl; alkynyl; haloalkyl; halo or alkoxy, or a group of formula —$N(R^4)(R^5)$ wherein $R^4$ and $R^5$ are independently hydrogen or $C_{1-6}$ alkyl or wherein $R^4$ and $R^5$ together represents —$(CH_2)_p$—, wherein p is 2, 3, 4 or 5.

4. A compound as claimed in any preceding claim wherein the value of n is 2.

5. An insecticidal composition comprising an insecticidally effective amount of a compound according to claim 1 in association with an insecticidally inert diluent or carrier.

6. A method of controlling insect pests at a locus which comprises application to the locus of an insecticidally effective amount of a composition as claimed in claim 5.

7. A compound according to claim 1 wherein the compound is 2-(morpholine-4-sulphonyl)-6-(methanesulphonyloxy) pyridine.

8. A compound according to claim 1 wherein the compound is 2-(azetidine-1-sulphonyl)-6-(methanesulphonyloxy)pyridine.

9. A compound according to claim 1 wherein the compound is 2-(piperidine-1-sulphonyl)-6-(methanesulphonyloxy)pyridine.

10. A compound according to claim 1 wherein the compound is 2-(pyrrole-1-sulphonyl)-7-(methanesulphonyloxy)pyridine.

11. A compound according to claim 1 wherein the compound is 2-(pyrrollidine-1-sulphonyl)-6-(methanesulphonyloxy)pyridine.

12. A compound according to claim 1 wherein the compound is 2-(thiomorpholine-4-sulphonyl)-6-(methanesulphonyloxy)pyridine.

13. A composition according to claim 5 wherein the group $R^3$ is $C_{1-4}$ alkyl, $C_{1-2}$ alkyl substituted with phenyl, $C_{1-6}$ alkyl haloalkyl, $C_{2-4}$ alkenyl, ethenyl, ethenyl substituted with a phenyl, phenyl, pyridyl, 2-thienyl, 3-thienyl, $C_{1-2}$ alkyl substituted with a substituted phenyl, ethenyl substituted with a substituted phenyl, substituted pyridyl wherein the substituents on the substituted phenyl and substituted pyridyl are alkyl; alkenyl; alkenyl; haloalkyl; halo or alkoxy, or a group of formula —$N(R^4)(R^5)$ wherein $R^4$ and $R^5$ independently hydrogen or $C_{1-6}$ alkyl or wherein $R^4$ and $R^5$ together represent —$(CH_2)_p$—, wherein p is 2, 3, 4 or 5.

14. A composition according to claim 13 wherein n is 2.

* * * * *